(12) United States Patent
Mun et al.

(10) Patent No.: US 10,864,037 B2
(45) Date of Patent: Dec. 15, 2020

(54) APPARATUS AND METHOD FOR DISCRIMINATING BIOLOGICAL TISSUE, SURGICAL APPARATUS USING THE APPARATUS

(71) Applicant: Research & Business Foundation SUNGKYUNKWAN UNIVERSITY, Suwon-si (KR)

(72) Inventors: Joung Hwan Mun, Seoul (KR); Su Hyun Youn, Suwon-si (KR); Ahnryul Choi, Seoul (KR)

(73) Assignee: Research & Business Foundation Sungkyunkwan University, Suwon-si (KR)

(*) Notice: Subject to any disclaimer, the term of this patent is extended or adjusted under 35 U.S.C. 154(b) by 613 days.

(21) Appl. No.: 15/203,872

(22) Filed: Jul. 7, 2016

(65) Prior Publication Data

US 2017/0007308 A1  Jan. 12, 2017

(30) Foreign Application Priority Data

Jul. 8, 2015 (KR) .................. 10-2015-0097370

(51) Int. Cl.
*A61B 18/14* (2006.01)
*A61B 18/00* (2006.01)

(52) U.S. Cl.
CPC .. *A61B 18/1445* (2013.01); *A61B 2018/0069* (2013.01); *A61B 2018/00607* (2013.01);
(Continued)

(58) Field of Classification Search
CPC ........... A61B 2018/00904; A61B 2018/00607; A61B 2018/00642; A61B 2018/00869;
(Continued)

(56) References Cited

U.S. PATENT DOCUMENTS

2002/0072686 A1* 6/2002 Hoey ................... A61B 5/0537
600/547
2007/0009160 A1* 1/2007 Loo ..................... G06K 9/0051
382/225
(Continued)

FOREIGN PATENT DOCUMENTS

KR   10-2008-0022527 A   3/2008
KR   10-2011-0123753 A   11/2011
(Continued)

OTHER PUBLICATIONS

Korean Office Action dated Sep. 21, 2016, in counterpart Korean Patent Application No. 10-2015-0097370 (7 pages in Korean).

*Primary Examiner* — Eun Hwa Kim
*Assistant Examiner* — Catherine Premraj
(74) *Attorney, Agent, or Firm* — NSIP Law

(57) ABSTRACT

The present disclosure relates to an apparatus and method for discriminating biological tissue, and a surgical apparatus using the same, the biological tissue discriminating method being capable of exactly discriminating the biological tissue by measuring an impedance value per frequency, teaching the measured impedance value per frequency in a single classifier according to learning algorithms that are different from one another having the measured impedance value per frequency as an input variable to discriminate the biological tissue, and re-teaching the biological tissue discriminated from each single classifier in a meta classifier to finally discriminate the biological tissue.

14 Claims, 8 Drawing Sheets

(52) U.S. Cl.
CPC ............. *A61B 2018/00642* (2013.01); *A61B 2018/00869* (2013.01); *A61B 2018/00875* (2013.01); *A61B 2018/00904* (2013.01); *A61B 2018/00994* (2013.01)

(58) Field of Classification Search
CPC ........... A61B 2018/00875; A61B 2018/00994; A61B 18/1445; A61B 5/053; A61B 5/0537; A61B 5/7264; A61B 5/7271
See application file for complete search history.

(56) References Cited

U.S. PATENT DOCUMENTS

| | | | |
|---|---|---|---|
| 2007/0239029 A1 | 10/2007 | Okabe et al. | |
| 2008/0125772 A1* | 5/2008 | Stone | A61B 18/1492 606/41 |
| 2010/0145328 A1* | 6/2010 | Hancock | A61B 18/18 606/33 |
| 2010/0191141 A1* | 7/2010 | Aberg | A61B 5/0531 600/547 |
| 2012/0326025 A1* | 12/2012 | Weinberger | G01N 33/57434 250/282 |
| 2016/0253466 A1* | 9/2016 | Agaian | G06N 3/0427 382/128 |

FOREIGN PATENT DOCUMENTS

| | | |
|---|---|---|
| KR | 10-1330883 B1 | 11/2013 |
| KR | 10-2014-0030680 A | 3/2014 |

* cited by examiner

APPARATUS AND METHOD FOR DISCRIMINATING BIOLOGICAL TISSUE, SURGICAL APPARATUS USING THE APPARATUS

This application claims the benefit under 35 USC § 119(a) of Korean Patent Application No. 10-2015-0097370 filed on Jul. 8, 2015 in the Korean Intellectual Property Office, the entire disclosure of which is incorporated herein by reference for all purposes.

FIELD

The present disclosure relates to an apparatus and method for discriminating a biological tissue, and a surgical apparatus using the same, and more particularly, to an apparatus and method capable of discriminating what kind of biological tissue the biological tissue of a surgery area is, using an impedance value measured from the biological tissue of the surgery area and automatically adjusting an output energy of the surgical apparatus according to the discriminated biological tissue, and a surgical apparatus using the same.

RELATED BACKGROUND ART

With the recent development of surgical apparatuses, surgical apparatuses capable of performing coagulation and cutting of a surgery area at the same time using various energies such as high frequency and/or ultrasonic wave signals and the like have been developed. As the demand for minimum invasion surgeries increases, these surgical apparatuses are being widely used especially in laparoscopic surgeries and thoracoscopic surgeries. The surgical method using such surgical apparatus is capable of performing coagulation and cutting topically at the same time, and thus has an advantage of minimizing bleeding of patients during surgeries and reducing the duration of surgeries.

This surgical apparatus is known to require adjustment of energy output according to physical properties of the biological tissue being treated. Here, in the case where an energy output that is weaker than a normal energy output is supplied to the tissue of a biological area being treated, there occurs a problem where the performance of cutting the tissue is degraded, making it impossible for the apparatus to operate properly, resulting in longer surgery hours. On the contrary, in the case where an energy output that is stronger than a normal energy output is supplied instead, there occurs a problem where the energy is transferred to surrounding areas, thereby causing sparks, burns and unnecessary coagulation, etc.

Since conventional surgical apparatuses require manual adjustment of energy output according to physical properties of biological tissues, doctors need to discriminate the type of the biological tissue while looking directly at images of the surgeries, and perform surgeries by repeating the process of manually adjusting the energy output according to the discriminated type of the biological tissues. These types of surgeries that depend on subjective thoughts of doctors have possibilities of causing trials and errors and prolonging the duration of surgeries due to unnecessary time spent.

Korean Patent Registration No. 10-1330883

SUMMARY OF THE INVENTION

Therefore, a purpose of the present disclosure is to solve such problems of prior art, that is, to provide an apparatus and method capable of exactly discriminating a biological tissue distributed within a biological tissue by measuring the impedance value that is unique for each biological tissue per frequency and then inputting the measured impedance values as a variable into a multi-classifier model, and a surgical apparatus using the same.

Further, another purpose of the present disclosure is to provide a surgical apparatus capable of automatically adjusting outputs of various energy being used such as high frequency or ultrasonic wave signals and the like according to discriminated biological tissue, thereby reducing the duration of surgeries and preventing surgeries from going wrong.

The tasks that the present disclosure intends to solve are not limited to the aforementioned tasks, and thus other tasks not mentioned above will be clearly understood by one skilled in the art based on the disclosure hereinafter.

According to an embodiment of the present disclosure, there is provided an apparatus for discriminating biological tissue, the apparatus including an impedance measurer having a first electrode for applying a signal having a frequency wave form to the biological tissue and a second electrode for receiving the signal that passed the biological tissue, and configured to measure an impedance magnitude and an impedance phase according to the frequency wave form of the biological tissue from the signal received; a base classifier including a plurality of single classifiers that are different from one another, configured to discriminate what kind of biological tissue the biological tissue is according to a machine learning algorithm having each of the impedance magnitude and the impedance phase measured while changing the frequency wave form as an input variable; and a meta classifier configured to finally discriminate what kind of biological tissue the biological tissue is according to the machine learning algorithm having each biological issue discriminated by the plurality of different single classifiers as an input variable.

Here, the impedance measurer may measure the impedance magnitude and the impedance phase in units of 10 kH between 10 kHz and 100 kHz of the frequency wave form.

Herein, the input variable may be selected differently for each of the single classifiers using a genetic algorithm method.

Here, the single classifier may be any one of a classifier according to a support vector machine (SVM) algorithm, a classifier according to a k-nearest neighbors (k-NN) algorithm, a classifier according to decision tree (DT) algorithm, a classifier according to a quadratic discriminant analysis (QDA) algorithm, and a classifier according to a random forest (RF) algorithm.

Here, the base classifier may include a classifier according to a support vector machine (SVM) algorithm, a classifier according to a quadratic discriminant analysis (QDA) algorithm, and a classifier according to a random forest (RF) algorithm.

Here, the meta classifier may be a classifier according to an artificial neural network (ANN) algorithm.

According to another embodiment of the present disclosure, there is provided a method for discriminating biological tissue, the method including (a) measuring an impedance magnitude and an impedance phase according to a frequency wave form of the biological tissue using a first electrode for applying a signal having the frequency wave form to the biological tissue and a second electrode for receiving the signal that passed the biological tissue; (b) discriminating what kind of biological tissue the biological tissue is by a plurality of single classifiers that are different from one another configured to discriminate what kind of biological tissue the biological tissue is according to a machine learning algorithm having each of the impedance magnitude and the impedance phase measured while changing the frequency wave form as an input variable; and (c) finally discriminating the biological tissue having each biological issue discriminated by the plurality of different single classifiers as an input variable in a meta classifier for discriminating what kind of biological tissue the biological tissue is according to the machine learning algorithm.

According to another embodiment of the present disclosure, there is provided an energy-based surgical apparatus for performing coagulation or cutting of biological tissue using energy generated by an electrical signal, the apparatus including a surgical device configured to transfer the energy to a surgery area; a biological tissue discriminating apparatus configured to discriminate what kind of biological tissue the biological tissue of the surgery area is; and an output control device configured to automatically adjust output of the energy according to the discriminated biological tissue.

Here, the biological tissue discriminating apparatus may include an impedance measurer having a first electrode for applying a signal having a frequency wave form to the biological tissue and a second electrode for receiving the signal that passed the biological tissue, and configured to measure from the signal received an impedance magnitude and an impedance phase according to the frequency wave form of the biological tissue; a base classifier including a plurality of single classifiers that are different from one another configured to discriminate what kind of biological tissue the biological tissue is according to a machine learning algorithm having each of the measured impedance magnitude and the impedance phase measured while changing the frequency wave form as an input variable; and a meta classifier configured to finally discriminate what kind of biological tissue the biological tissue is according to the machine learning algorithm having each biological issue discriminated by the plurality of different single classifiers as an input variable.

Here, the impedance measurer may measure the impedance magnitude and the impedance phase in units of 10 kH between 10 kHz and 100 kHz of the frequency wave form.

Here, the input variable may be selected differently for each of the single classifiers using a genetic algorithm method.

Here, the single classifier may be any one of a classifier according to a support vector machine (SVM) algorithm, a classifier according to a k-nearest neighbors (k-NN) algorithm, a classifier according to decision tree (DT) algorithm, a classifier according to a quadratic discriminant analysis (QDA) algorithm, and a classifier according to a random forest (RF) algorithm.

Here, the base classifier may include a classifier according to a support vector machine (SVM) algorithm, a classifier according to a quadratic discriminant analysis (QDA) algorithm, and a classifier according to a random forest (RF) algorithm.

Here, the meta classifier may be a classifier according to an artificial neural network (ANN) algorithm.

Here, the energy may be generated by a high frequency signal or an ultrasonic wave signal.

The apparatus and method for discriminating biological tissue according to the present disclosure have an advantage of exactly discriminating the biological tissue having a nonlinear distribution by measuring the impedance values that is unique for each biological tissue according to frequency and then inputting the measured impedance values as a variable into a multi-classifier model, and a surgical apparatus using the same.

Further, there is also an advantage of further improving the exactness of discrimination than when using only the single classifier since the results of discrimination by the plurality of single classifiers are inputted into the meta classifier again and the biological tissue is finally discriminated.

Further, there is also an advantage of preventing erroneous surgeries and reducing the duration of the surgeries since coagulation and cutting may be conducted while automatically adjusting the energy output of high frequency waves and/or ultrasonic wave signals and the like being used according to the discriminated biological tissue.

BRIEF DESCRIPTION OF THE DRAWINGS

Example embodiments will now be described more fully hereinafter with reference to the reference to the accompanying drawings; however, they may be embodied in different forms and should not be construed as limited to the embodiments set forth herein. Rather, these embodiments are provided so that this disclosure will be thorough and complete, and will fully convey the scope of the example embodiments to those skilled in the art.

In the drawing figures, dimensions may be exaggerated for clarity of illustration. It will be understood that when an element is referred to as being "between" two elements, it can be the only element between the two elements, or one or more intervening elements may also be present between two elements. Like reference numerals refer to like elements throughout.

DETAILED DESCRIPTION

Hereafter, the apparatus and method for discriminating biological tissue and a surgical apparatus using the same according to an embodiment of the present disclosure will be explained with reference to the drawings attached. The embodiment should not be construed as limited to the scope of protection of the claims attached hereto but as an example.

First, prior to explaining the apparatus and method for discriminating biological tissue and a surgical apparatus using the same according to the embodiment of the present disclosure, an experiment process of discriminating a biological tissue according to the present disclosure will be explained and the results will be analyzed in order to improve understanding of the present disclosure.

1. Types of Electrodes for Measuring Impedance of Biological Tissue

Figure 1:
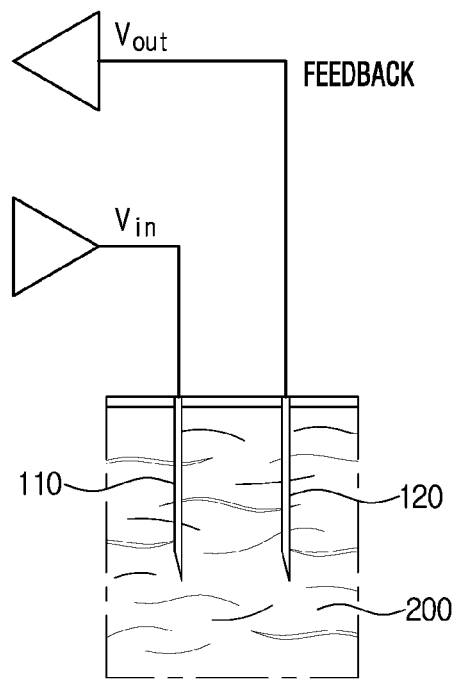
FIG. 1 is a view provided to explain a principle of measuring an impedance using a bipolar type electrode.
Figure 2A:
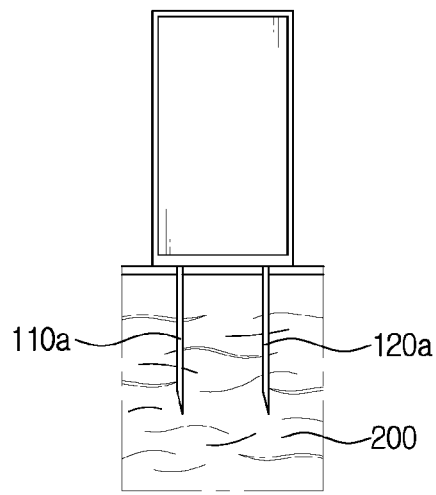
FIGS. 2A, 2B and 2C respectively illustrate three types of electrodes used in experiments for discriminating a biological tissue according to the present disclosure.
Figure 2B:
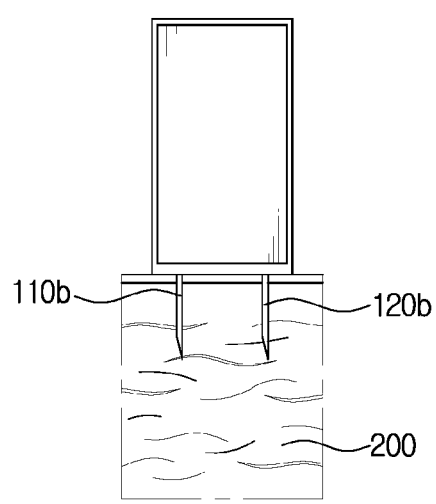
Figure 2C:
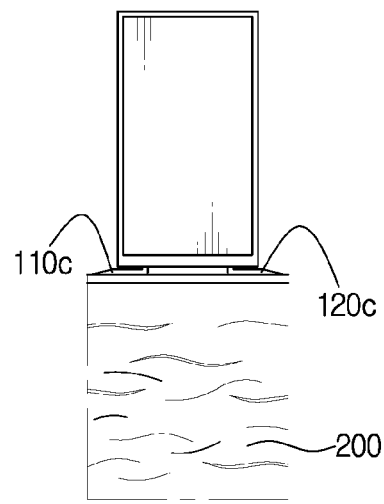

FIG. 1 is a view provided to explain a principle of measuring an impedance using a bipolar type electrode, and FIGS. 2A, 2B and 2C respectively illustrate three types of electrodes used in experiments for discriminating a biological tissue according to the present disclosure.

The present disclosure discriminates a biological tissue 200 using an impedance magnitude and/or impedance phase among unique electrical characteristics of the biological tissue 200. Therefore, it is necessary to measure the impedance value of the biological tissue 200. In experiments according to the present disclosure, three types of electrodes were used to measure the impedance value.

First, the principle of measuring the impedance using the bipolar type electrode 110, 120 will be explained hereinafter with reference to FIG. 1. The first electrode 110 applies to the contacted biological tissue 200 a current or a voltage signal having a certain frequency wave form, and the signal that passed the biological tissue 200 is fed back to the second electrode 120. Using this signal fed back, the impedance magnitude and the impedance phase of the biological tissue 200 may be obtained. Hereinafter, the impedance magnitude and/or the impedance phase will be simply referred to as the impedance value.

Here, the impedance value differs depending on the frequency. In the experiments of the present disclosure, impedances were measured while changing the frequency. This will be explained in detail hereinafter.

FIGS. 2A, 2B and 2C respectively illustrate three types of electrodes used in the experiments. FIGS. 2A and 2B illustrate invasive type electrodes 110a, 120a, 110b, 120b (hereinafter, FIG. 2A will be referred to as electrode type (a), and FIG. 2B will be referred to as electrode type (b)), while FIG. 2C illustrates noninvasive type electrodes 110c, 120c (hereinafter referred to as electrode type (c)). Here, in FIG. 2A, the invading depth of the electrode is 6 mm, and in FIG. 2B, the invading depth of the electrode is 3 mm. In all of FIGS. 2A, 2B and 2C, the distance between the electrodes are the same, that is, 2.5 mm.

2. Biological Tissue Subject to Experiments

A biological tissue 200 of a pig was used as the subject of the experiments. First, fat and muscle tissues accounting for the largest proportion of a human body were selected. According to prior researches, even one tissue can have heterogeneous properties for different areas of the tissue, and thus in the experiments, the fat and muscle tissues were extracted from a neck area and an abdomen area. Further, a liver tissue that is a major organ inside an abdominal cavity where a laparoscopic surgery is performed and a lung tissue that is a major organ inside a thoracic cavity were selected and extracted. Therefore, in the present experiments, six biological tissues 200 including the muscle (abdomen area), muscle (neck area), fat (abdomen area), fat (neck area), liver and lung were used as subjects from which the impedance value was measured, respectively.

3. Measurement of Impedance Value

In the experiments, an impedance value of each of the six biological tissues 200 was measured using the three types of electrodes 110, 120 explained above with reference to FIG. 2A, FIG. 2B and FIG. 2C. Here, the impedance values were measured as in <table 1> below while changing the frequency ranges of the electrode signal in units of 10 kH from 10 kH to 100 kHz.

TABLE 1

| 10 kHz | | 20 kHz | | 30 kHz | | 40 kHz | | 50 kHz | | 60 kHz | | 70 kHz | | 80 kHz | | 90 kHz | | 100 kHz | |
|---|---|---|---|---|---|---|---|---|---|---|---|---|---|---|---|---|---|---|---|
| |z| | P | |z| | P | |z| | P | |z| | P | |z| | P | |z| | P | |z| | P | |z| | P | |z| | P | |z| | P |

(Here, |z| is the impedance magnitude and P is the impedance phase.)

That is, since the impedance magnitude and the impedance phase are measured while changing the frequency in units of 10 kH from 10 kH to 100 kHz, it is possible to measure a total of 20 data for each biological tissue 200. Further, the 20 data were measured per three types of electrodes 110, 120 aforementioned.

Figure 3A:
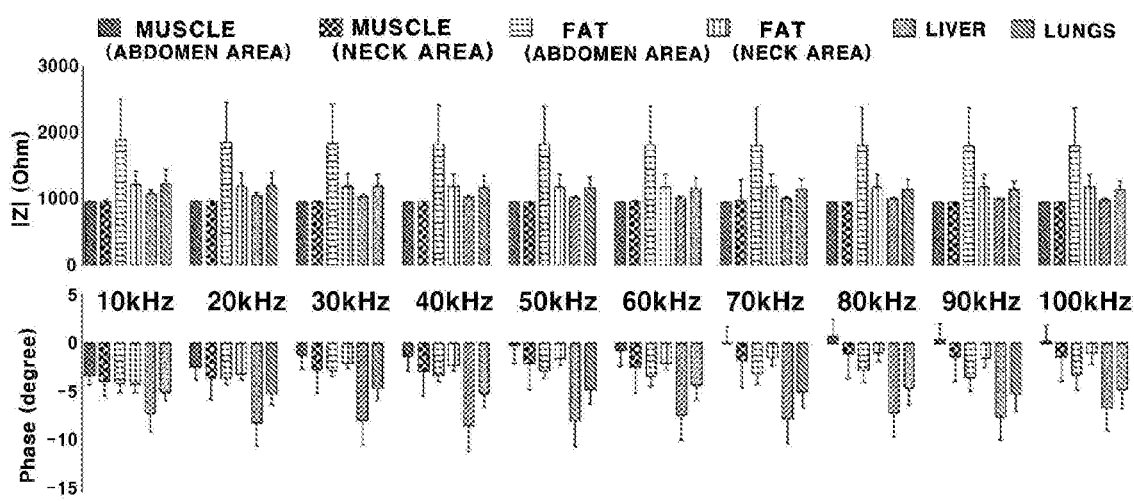
FIGS. 3A, 3B and 3C respectively illustrate an impedance value measured of six types of biological tissues using the three types of electrodes of FIGS. 2A, 2B and 2C.
Figure 3B:
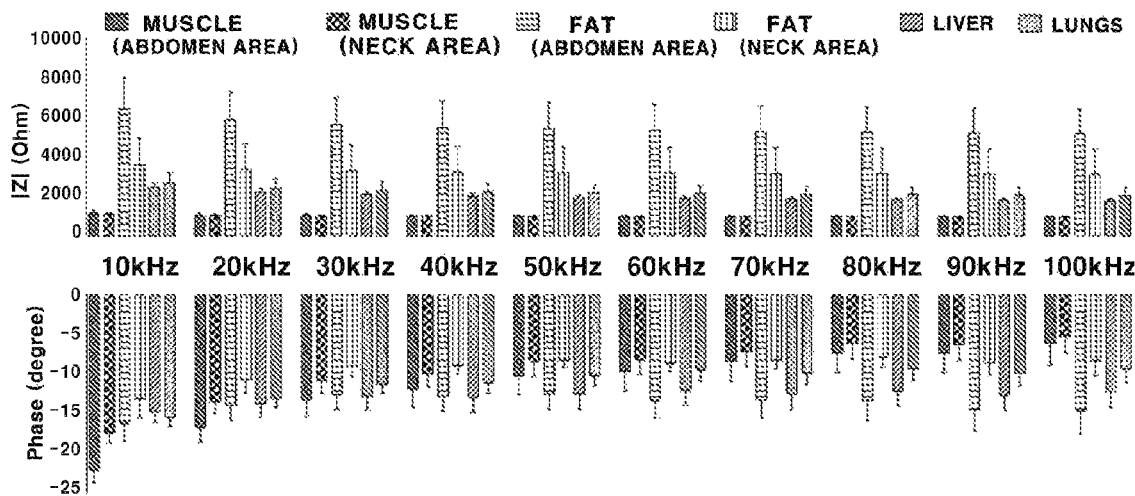
Figure 3C:
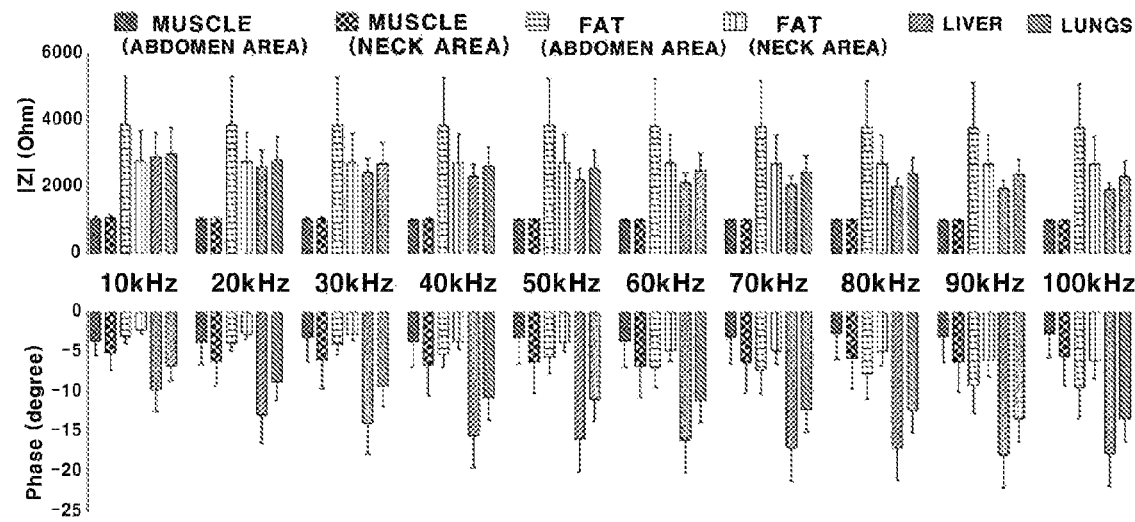

FIG. 3A, FIG. 3B and FIG. 3C are views each illustrating the impedance value measured of the six types of biological tissues using the three types of electrodes of FIG. 2A, FIG. 2B and FIG. 2C, respectively, in the experiments for discriminating the biological tissue according to the present disclosure.

FIG. 3A, FIG. 3B and FIG. 3C are views each illustrating the impedance value measured in units of 10 kHz frequency from 10 kHz to 100 kHz as in the table using the electrode 110, 120 of the types of FIG. 2A, FIG. 2B and FIG. 2C, respectively. In each of FIG. 3A, FIG. 3B and FIG. 3C, the graphs in the upper part illustrates the impedance magnitude of each area measured per frequency, and the graphs in the lower part illustrates the impedance phase of each area measured per frequency. Each graph illustrated per frequency illustrates from the left the measurement value for the muscle tissue (abdominal area), muscle tissue (neck area), fat tissue (neck area), liver tissue and lung tissue that are the aforementioned six biological tissues.

4. Discrimination of Biological Tissue Using Multi-Classifier

Figure 4:
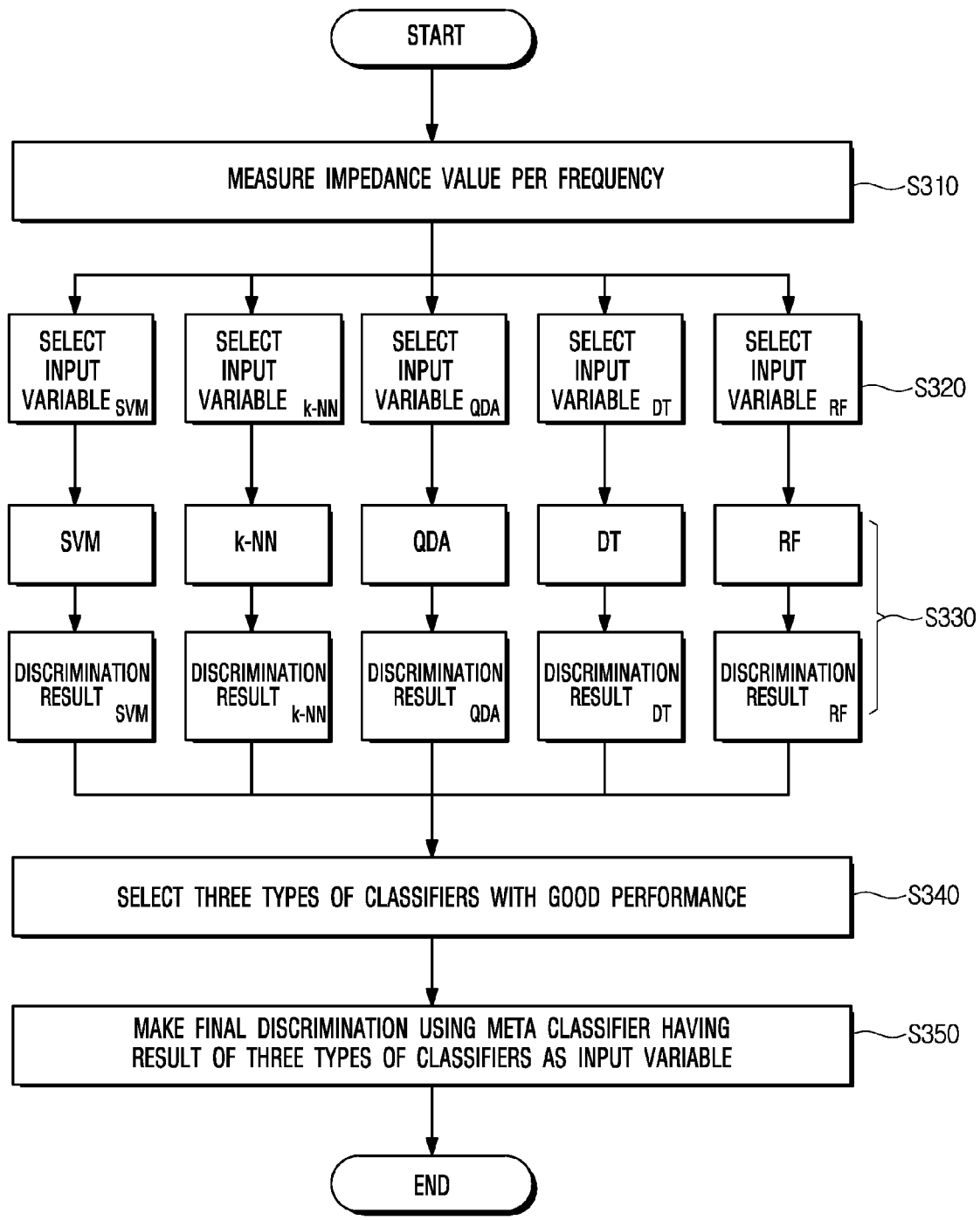
FIG. 4 is a flowchart of a process for discriminating the biological tissue in an experiment of discriminating a biological tissue according to the present disclosure.

FIG. 4 is a flowchart illustrating a process of discriminating a biological tissue in an experiment for discriminating the biological tissue according to the present disclosure.

First, impedance values of the six types of the biological tissue 200 are measured while changing the frequency as aforementioned (S310).

From prior studies, it is known that an impedance value of the biological tissue 200 has a nonlinear distribution, and thus in the present experiment, the biological tissue 200 was discriminated using the machine learning algorithm having the impedance values measured per frequency as the input variable. For reference, the machine learning is known as a technology that is associated with an ability to learn new information and efficiently use the obtained information, and specific and various algorithm methods are known.

In the present experiment, the biological tissue 200 was discriminated by using the impedance value measured as the input variable in each single classifier of the classifier according to a support vector machine (SVM) algorithm, a classifier according to a k-NN (k-nearest neighbors) algorithm, a classifier according to a decision tree (DT) algorithm, a quadratic discriminant analysis (QDA) algorithm, and a random forest (RF) algorithm (S330).

Here, in order to improve the discriminating performance of each single classifier, the input variable was selected differently per classifier (S320). That is, instead of using the twenty impedance values of the aforementioned <table 1> as the input variable of each classifier in a same manner, an input variable that could maximize the performance was selected per classifier and was used as the input variable of each single classifier. Here, the genetic algorithm method was used as the method for selecting the input variable.

<Table 2> below illustrates the input variables selected by the genetic algorithm per single classifier.

| (Unit: 10 kHz) | Electrode type (a) | | Electrode type (b) | | Electrode type (c) | |
|---|---|---|---|---|---|---|
| | \|z\| | P | \|z\| | P | \|z\| | P |
| SVM | 2, 3, 5 | 1, 3, 4, 6, 8 | 4, 6, 7, 8 | 1, 2, 4, 5, 6, 7, 8, 9 | 1, 3, 6, 8, 9 | 1, 2, 4, 8, 9 |
| k-NN | 1, 2, 3, 4, 6, 7, 10 | All | 1, 6, 8, 10 | 1, 2, 3, 6, 7, 8 | 1, 3, 4, 5, 6, 7, 8, 9, 10 | 1, 2, 3, 4, 5, 6, 7, 8 |
| DT | 1, 2, 3, 4, 7, 8, 9 | 1, 2, 4, 5, 6, 7, 8, 9, 10 | 5, 7, 8, 9, 10 | 1, 6, 10 | All | All |
| QDA | 2, 8, 10 | 1, 2, 9, 10 | 10 | 1, 2, 3, 4, 5, 6, 8, 10 | 1, 2, 6, 7, 8, 9, 10 | All |
| RF | 2, 3, 4, 5, 6, 7, 8, 9, 10 | 1, 5, 6, 7, 9, 10 | All | 1, 2, 5, 6, 7, 8, 9, 10 | 1, 2, 3, 4, 6, 7, 8, 9, 10 | 1, 3, 4, 5, 6, 7, 8, 9, 10 |

For example, in the electrode type (a) of the classifier according to the SVM algorithm in <Table 2>, 2, 3 and 5 refer to the impedance magnitudes when the frequency in <Table 1> is 20 kHz, 30 kHz and 50 kHz, respectively, and in the electrode type (a) of the classifier according to the SVM algorithm, 1, 3, 4, 6 and 8 refer to the impedance phases when the frequency in <Table 1> is 10 kHz, 30 kHz, 40 kHz, 60 kHz and 80 kHz, respectively.

Therefore, in the electrode type (a) of the classifier according to the SVM algorithm, the performance of the classifier shows the maximum level when the impedance magnitude when the frequency is 20 kHz, 30 kHz and 50 kHz and the impedance phase when the frequency is 20 kHz, 30 kHz and 50 kHz selected by the genetic algorithm are the input variables of the SVM algorithm.

Even when the same data is the input variable, different results may occur per single classifier, and thus there are limitations to the exactness in classifying multi-dimensional classes with only the single classifier. Therefore, the present experiment used the multi-classifier model that re-teaches the classification results through five different single classifiers to a meta classifier to finally discriminate the biological tissue 200 (S350), in order to improve the exactness of discriminating the biological tissue 200. Here, the meta classifier used the artificial neural network (ANN) algorithm.

Here, when using the results discriminated from the aforementioned five single classifiers, not the results discriminated from all five single classifiers were used, but the results from three single classifiers were used as input variables of the metal classifier. As aforementioned, the discrimination results may differ even per single classifier, and it is possible to estimate the discriminating performance per single classifier, select the three types of classifiers with the highest discriminating performance (S340) and have the results as the input variables of the meta classifier, thereby improving the discriminating performance. As a result of analyzing the discriminating performance of each single classifier in the present experiment, a classifier according to the SVM algorithm, a classifier according to a QDA algorithm, and a classifier according to an RF algorithm were selected.

The result of teaching the discrimination results from the three aforementioned classifiers to the meta classifier again as the input variable is the finally discriminated biological tissue (S350).

5. Discrimination Result

<Table 3> below shows the results of the present experiment per electrode type of FIG. 2A, FIG. 2B and FIG. 2C.

TABLE 3-1

| | Experiment results of electrode type (a) | | | | | | | |
|---|---|---|---|---|---|---|---|---|
| | Muscle (abdomen area) | Fat (abdomen area) | Muscle (neck area) | Fat (neck area) | Liver | Lungs | Total | PPV (%) |
| Muscle (abdomen area) | 132 | | 11 | | 1 | | 144 | 91.67 |
| Fat (abdomen area) | | 123 | 1 | 13 | | | 137 | 89.78 |
| Muscle (neck area) | 18 | | 138 | | | | 156 | 88.46 |
| Fat (neck area) | | 26 | | 135 | | | 161 | 83.85 |
| Liver | | | | 1 | 148 | 2 | 151 | 98.01 |
| Lungs | | 1 | | 1 | 1 | 148 | 151 | 98.01 |
| Total | 150 | 150 | 150 | 150 | 150 | 150 | 900 | |
| Sensitivity (%) | 88.00 | 82.00 | 92.00 | 90.00 | 98.67 | 98.67 | | |

TABLE 3-2

Experiment results of electrode type (b)

| | Muscle (abdomen area) | Fat (abdomen area) | Muscle (neck area) | Fat (neck area) | Liver | Lungs | Total | PPV (%) |
|---|---|---|---|---|---|---|---|---|
| Muscle (abdomen area) | 148 | | | | | | 148 | 100.00 |
| Fat (abdomen area) | 1 | 147 | | 3 | | 1 | 152 | 96.71 |
| Muscle (neck area) | 1 | | 150 | 1 | | | 152 | 98.68 |
| Fat (neck area) | | 3 | | 146 | | | 149 | 97.99 |
| Liver | | | | | 149 | 1 | 150 | 99.33 |
| Lungs | | | | | 1 | 148 | 149 | 99.33 |
| Total | 150 | 150 | 150 | 150 | 150 | 150 | 900 | |
| Sensitivity (%) | 98.67 | 98.00 | 100.00 | 97.33 | 99.33 | 98.67 | | |

TABLE 3-3

Experiment results of electrode type (3)

| | Muscle (abdomen area) | Fat (abdomen area) | Muscle (neck area) | Fat (neck area) | Liver | Lungs | Total | PPV (%) |
|---|---|---|---|---|---|---|---|---|
| Muscle (abdomen area) | 117 | | 19 | 1 | | | 137 | 85.40 |
| Fat (abdomen area) | 1 | 135 | | 14 | | | 150 | 90.00 |
| Muscle (neck area) | 32 | | 131 | | | | 163 | 80.37 |
| Fat (neck area) | | 15 | | 135 | | | 150 | 90.00 |
| Liver | | | | | 143 | 4 | 147 | 97.28 |
| Lungs | | | | | 7 | 146 | 153 | 95.42 |
| Total | 150 | 150 | 150 | 150 | 150 | 150 | 900 | |
| Sensitivity (%) | 78.00 | 90.00 | 87.33 | 90.00 | 95.33 | 97.33 | | |

The experiment results are results of experiments conducted per electrode type 110, 120 on 150 samples extracted from the same biological tissue 200. For example, <Table 3-1> shows results of discriminating 150 samples extracted from each biological tissue 200 using the electrode type (a) 110a, 120a. In the experiment for the muscle in abdomen area, 132 of the total of 150 samples were discriminated as the muscle in abdomen area, and 18 samples were discriminated as the muscle in neck area, thereby showing 88.00% of discriminating rate.

One can see that the case of using an invasive type electrode ((a), (b)) 110a, 120a, 110b, 120b shows higher discrimination exactness compared to the non-invasive type electrode ((c)) 110c, 120c overall. Especially, the exactness was very high when using the (b) type electrode 110b, 120b.

Hereafter, explanation will be made on the apparatus and method for discriminating biological tissue according to an embodiment of the present disclosure based on the aforementioned information on the experiments according to the present disclosure.

Figure 5:
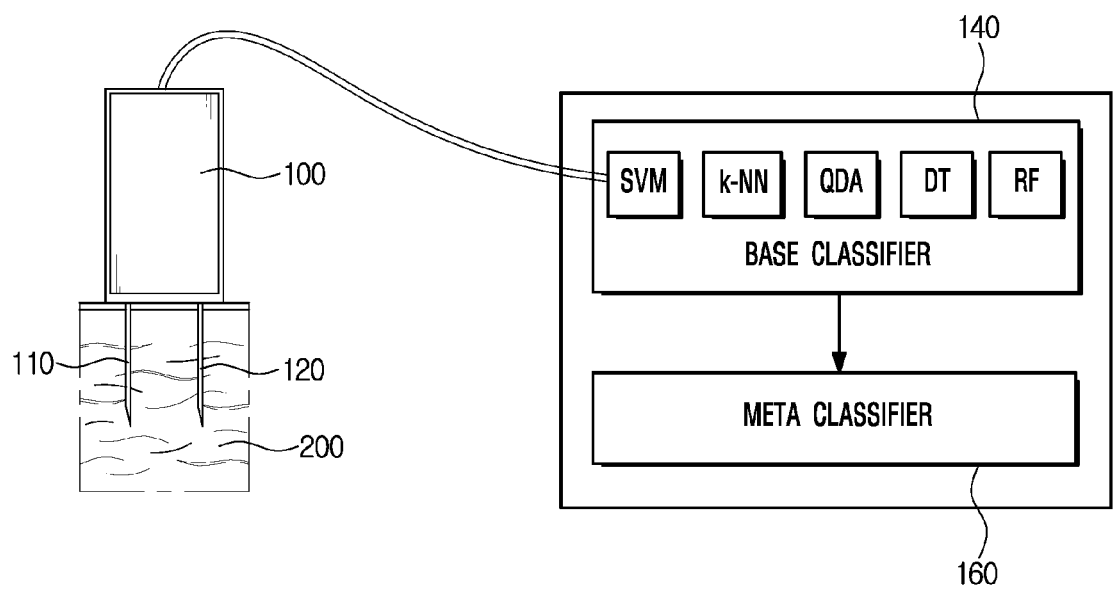
FIG. 5 is a schematic view illustrating an apparatus for discriminating a biological tissue according to an embodiment of the present disclosure.

FIG. 5 is a schematic view illustrating the apparatus of discriminating biological tissue according to an embodiment of the present disclosure.

The apparatus of discriminating biological tissue according to the present disclosure may include an impedance measurer 100, a base classifier 140 and a meta classifier 160.

The impedance measurer 100, as aforementioned with reference to FIG. 1, FIG. 2A, FIG. 2B and FIG. 2C, includes the first electrode 110 for applying a current or voltage signal having a certain frequency wave form to the biological tissue 200 and the second electrode 120 that is fed back with the signal that passed the biological tissue 200 and receives the signal again, and the impedance measurer 100 may measure the impedance magnitude and impedance phase of the biological tissue 200 according to the frequency wave form from the fed back signal. The type of the electrode 110, 120 is not limited to that mentioned above with reference to FIG. 2A, FIG. 2B and FIG. 2C, and thus may differ in various ways by changing the invading length and the distance between the two electrodes and the like regardless of whether the electrode is an invasive type or a non-invasive type.

Here, the impedance measurer 100 may measure the impedance value while changing the frequency wave form, desirably changing the frequency wave form in units of 10 kHz from 10 kHz to 100 Hz.

The base classifier 140 discriminates the biological tissue 200 in learning using the machine learning algorithm using the impedance value per frequency wave form measured in the impedance measurer 100. Here, the present disclosure discriminates the biological tissue through each of single classifiers having different machine learning algorithms.

Examples of the machine learning algorithms include the SVM algorithm, k-NN algorithm, DT algorithm, QDA algorithm and RF algorithm and the like, but without limitation, and thus various well known machine learning algorithms may be used.

The apparatus for discriminating biological tissue according to an embodiment of the present disclosure may use three single classifiers as the base classifier 140. It is desirable to select the classifier according to the SVM algorithm, the classifier according to the QDA algorithm and the classifier according to the RF algorithm, but there is no limitation thereto.

Here, in the present disclosure, when teaching for discriminating biological tissue using each single classifier, it is possible to set different input variables that enable the best performance for each single classifier instead of setting the same input variable. Here, the variable enabling the best performance for each single classifier may be selected using the genetic algorithm method.

The meta classifier 140 re-teaches with the machine learning algorithm having the result discriminated from different single classifiers as the input variable again, thereby finally discriminating the biological tissue 200. As aforementioned, the biological tissue discriminated from each single classifier may differ due to the difference of performance of the single classifier. Therefore, in the present disclosure, it is possible to re-teach to the metal classifier 160 having the biological tissue discriminated from each single classifier as the input variable to finally discriminate the biological tissue 200, thereby improving the discriminating performance. Here, the ANN algorithm may be used as the algorithm to be used in the meta classifier 160.

Figure 6:
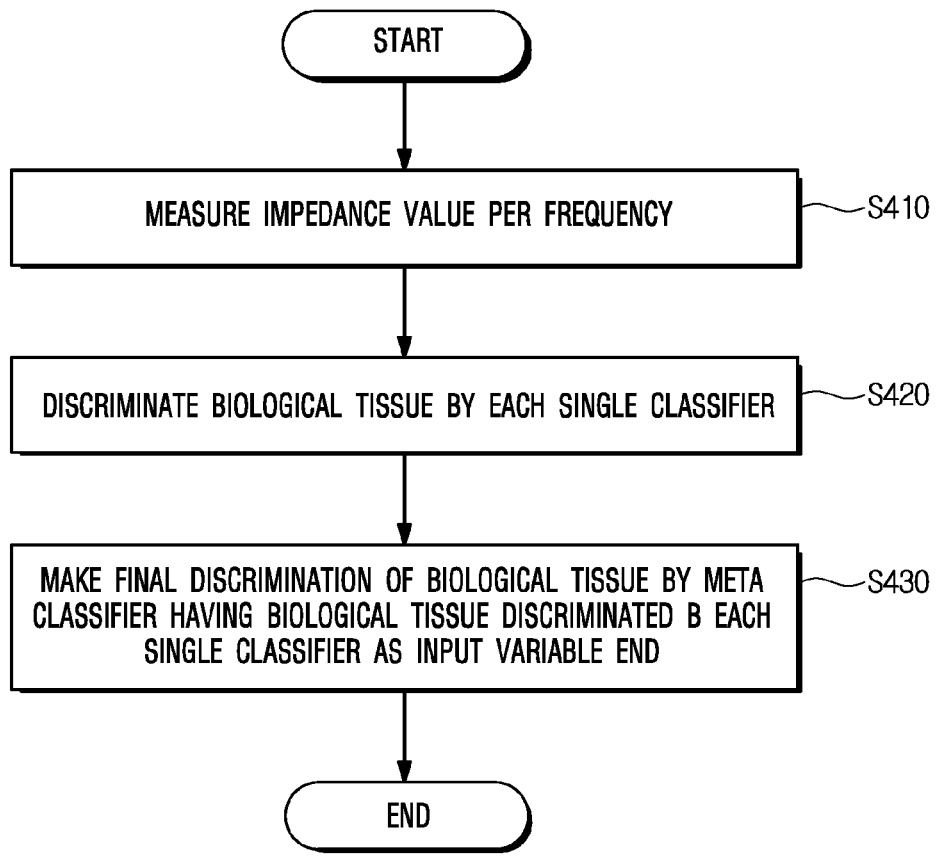
FIG. 6 is a flowchart of a method for discriminating a biological tissue according to an embodiment of the present disclosure.

FIG. 6 is a flowchart illustrating a method for discriminating biological tissue according to an embodiment of the present disclosure.

The method for discriminating biological tissue according to an embodiment of the present disclosure first measures the impedance value using the first electrode 110 and the second electrode 120 of the impedance measurer 100 (S410). Desirably, it is possible to measure the impedance value in units of 10 kHz between 10 kHz and 100 kHz while changing the frequency wave form.

Then, by teaching through each single classifier constituting the base classifier 140 having the impedance value measured while changing the frequency wave form as in the input variable, each biological tissue 200 is discriminated (S420). Here, as aforementioned, the input variable may differ per single classifier.

Then, by re-teaching the biological tissue 200 discriminated through each single classifier to the metal classifier 160, it is finally discriminated what kind of biological tissue the biological tissue 200 measured by the impedance measurer 100 is (S430).

Hereinafter, explanation will be made on a surgical apparatus according to an embodiment of the present disclosure.

Figure 7:
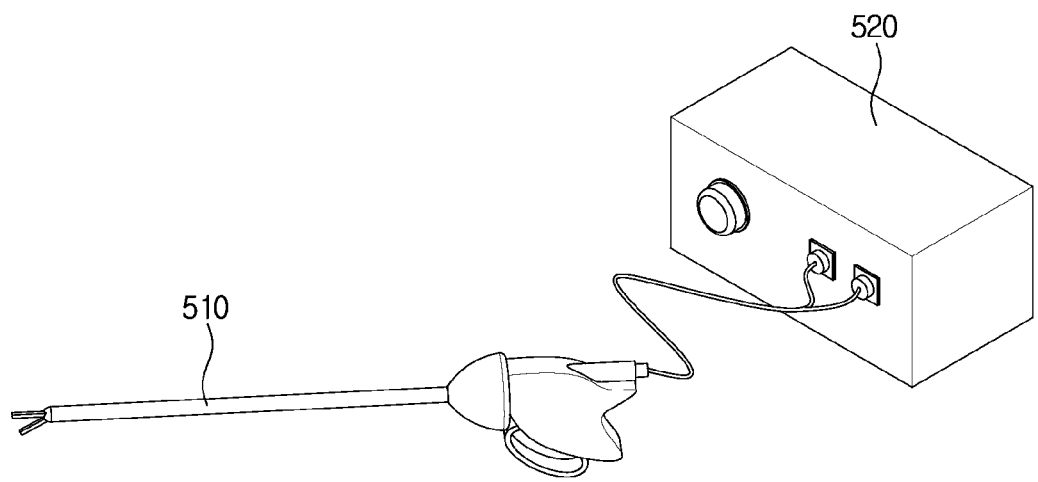
FIG. 7 is a view illustrating a surgical apparatus according to an embodiment of the present disclosure.

FIG. 7 is a view illustrating the surgical apparatus according to an embodiment of the present disclosure.

The surgical apparatus according to the embodiment of the present disclosure may include a surgical apparatus 510, a biological discriminating apparatus (not illustrated) and an output control apparatus 520.

The surgical device 510 may transmit energy such as a high frequency wave or ultrasonic wave signal and the like generated in a signal generating device in a surgery area so that the surgery area may be coagulated or cut. For example, the high frequency signal uses the principle where it directly passes the human body so that heat generated in the touched tissue can be used, whereas when using the ultrasonic wave signal, the signal is converted into mechanical(physical) motion so that the friction heat generated in the grasped tissue may be used, and thus the high frequency signal or the ultrasonic wave signal may be used to cut and coagulate a surgery area.

Disposed at one end of the surgical apparatus 510 or close to the surgical apparatus 510, the apparatus for discriminating biological tissue (not illustrated) discriminates what kind of biological tissue the biological tissue 200 is prior to conducting a surgery using the surgical apparatus 510. The apparatus for discriminating biological tissue (not illustrated) according to the present disclosure is the same as the apparatus for discriminating biological tissue mentioned above with reference to FIG. 5, and thus specific explanation thereon will be omitted.

The output control apparatus 520 automatically adjusts energy output of the high frequency or ultrasonic wave signal and the like being used of the surgical apparatus 510 according to the biological tissue discriminated according to the apparatus for discriminating biological tissue (not illustrated).

As aforementioned, in the present disclosure, the performance of discriminating biological tissue 200 may be significantly improved using the multi-classifier, and the energy of the surgical apparatus 510 may be automatically adjusted according to the discriminated biological tissue, thereby reducing preventing erroneous surgeries and reducing the surgery time.

In the drawings and specification, there have been disclosed typical embodiments of the invention, and although specific terms are employed, they are used in a generic and descriptive sense only and not for purposes of limitation. It will be understood by those of ordinary skill in the art that various changes in form and details may be made therein without departing from the spirit and scope of the present invention as defined by the following claims.

REFERENCE NUMBERS

100: IMPEDANCE MEASURER
110a, 110b, 110c: FIRST ELECTRODE
120a, 120b, 120c: SECOND ELECTRODE
140: BASE CLASSIFIER
160: META CLASSIFIER
200: BIOLOGICAL TISSUE
510: SURGICAL APPARATUS
520: OUTPUT CONTROL DEVICE

The invention claimed is:

1. An apparatus for discriminating biological tissue, the apparatus comprising:
   an impedance measurer comprising a first electrode for applying a signal to the biological tissue and a second electrode for receiving the signal, the impedance measurer being configured to measure an impedance magnitude and an impedance phase from the received signal;
   a base classifier comprising a plurality of single classifiers that are different from one another, each of the plurality of single classifiers being configured to discriminate the biological tissue according to a first machine learning algorithm, wherein the impedance magnitude and the impedance phase are used as input variables of the plurality of single classifiers, wherein the input variables of the plurality of single classifiers are selected to be different for each of the plurality of single classifiers using a genetic algorithm method, and wherein one or more classifiers among the plurality of single classifiers are selected based on discrimination performance, wherein the selected one or more classifiers is a subset of the plurality of single classifiers, the subset having the highest discrimination performance among the plurality of single classifiers; and
a meta classifier configured to finally discriminate the biological tissue according to a second machine learning algorithm, wherein results of the selected one or more classifiers are used as input variables of the second machine learning algorithm.

2. The apparatus according to claim 1, wherein the impedance measurer is further configured to measure the impedance magnitude and the impedance phase with a frequency of the signal being adjusted by units of 10 kH between 10 kHz and 100 kHz.

3. The apparatus according to claim 1, wherein the plurality of single classifiers comprises a classifier according to any one or any combination of any two or more of a support vector machine (SVM) algorithm, a k-nearest neighbors (k-NN) algorithm, a decision tree (DT) algorithm, a quadratic discriminant analysis (QDA) algorithm, and a random forest (RF) algorithm.

4. The apparatus according to claim 1, wherein the base classifier comprises a classifier according to any one or any combination of any two or more of a support vector machine (SVM) algorithm, a quadratic discriminant analysis (QDA) algorithm, and a random forest (RF) algorithm.

5. The apparatus according to claim 1, wherein the meta classifier comprises a classifier according to an artificial neural network (ANN) algorithm.

6. A method for discriminating biological tissue, the method comprising:
measuring an impedance magnitude and an impedance phase using a first electrode for applying a signal to the biological tissue and a second electrode for receiving the signal;
discriminating the biological tissue by a plurality of single classifiers that are different from one another and configured to discriminate the biological tissue according to a first machine learning algorithm, wherein the impedance magnitude and the impedance phase are used as input variables of the plurality of single classifiers, wherein the input variables of the plurality of single classifiers are selected to be different for each of the plurality of single classifiers using a genetic algorithm method, and wherein one or more classifiers among the plurality of single classifiers are selected based on discrimination performance, wherein the selected one or more classifiers is a subset of the plurality of single classifiers, the subset having the highest discrimination performance among the plurality of single classifiers; and
finally discriminating the biological tissue by a meta classifier according to a second machine learning algorithm, wherein results of the selected one or more classifiers are used as input variables of the second machine learning algorithm.

7. An apparatus for performing coagulation or cutting of biological tissue, the apparatus comprising:
a surgical device configured to output energy to a surgery area;
a biological tissue discriminating device configured to make a final discrimination of biological tissue of the surgery area; and
an output control device configured to automatically adjust the output of energy based on the final discrimination,
wherein the biological tissue discriminating device comprises
an impedance measurer comprising a first electrode for applying a signal to the biological tissue and a second electrode for receiving the signal, the impedance measurer being configured to measure an impedance magnitude and an impedance phase from the received signal,
a base classifier comprising a plurality of single classifiers that are different from one another, each of the plurality of single classifiers being configured to discriminate the biological tissue according to a first machine learning algorithm, wherein the impedance magnitude and the impedance phase are used as input variables of the plurality of single classifiers, wherein the input variables of the plurality of single classifiers are selected to be different for each of the plurality of single classifiers using a genetic algorithm method, and wherein one or more classifiers among the plurality of single classifiers are selected based on discrimination performance, wherein the selected one or more classifiers is a subset of the plurality of single classifiers, the subset having the highest discrimination performance among the plurality of single classifiers, and
a meta classifier configured to make the final discrimination of the biological tissue according to a second machine learning algorithm, wherein results of the selected one or more classifiers are used as input variables of the second machine learning algorithm.

8. The apparatus according to claim 7, wherein the impedance measurer is further configured to measure the impedance magnitude and the impedance phase with a frequency of the signal being adjusted by units of 10 kH between 10 kHz and 100 kHz.

9. The apparatus according to claim 7, wherein the plurality of single classifiers comprise a classifier according to any one or any combination of any two or more of a support vector machine (SVM) algorithm, a k-nearest neighbors (k-NN) algorithm, a decision tree (DT) algorithm, a quadratic discriminant analysis (QDA) algorithm, and a random forest (RF) algorithm.

10. The apparatus according to claim 7, wherein the base classifier comprises a classifier according to any one or any combination of any two or more of a support vector machine (SVM) algorithm, a quadratic discriminant analysis (QDA) algorithm, and a random forest (RF) algorithm.

11. The apparatus according to claim 7, wherein the meta classifier comprises a classifier according to an artificial neural network (ANN) algorithm.

12. The apparatus according to claim 7, wherein the energy is generated by an ultrasonic wave signal.

13. The apparatus of claim 1, wherein the second machine learning algorithm re-teaches classification results through the plurality of single classifiers to the meta classifier to finally discriminate the biological tissue.

14. The apparatus of claim 1, wherein the impedance measurer is further configured to measure the impedance magnitude by incrementally changing a frequency of the signal between a minimum frequency and a maximum frequency.

* * * * *